US012610487B2

(12) United States Patent
Day et al.

(10) Patent No.: US 12,610,487 B2
(45) Date of Patent: Apr. 21, 2026

(54) SEALED PACKAGE INCLUDING ELECTRONIC DEVICE AND POWER SOURCE

(71) Applicant: Medtronic, Inc., Minneapolis, MN (US)

(72) Inventors: John K. Day, Chandler, AZ (US); Michael J. Nidelkoff, Eagan, MN (US); Kris A. Peterson, Minneapolis, MN (US); Andrew J. Ries, Lino Lakes, MN (US); David A. Ruben, Mesa, AZ (US); Craig L. Wiklund, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 1498 days.

(21) Appl. No.: 17/013,609

(22) Filed: Sep. 6, 2020

(65) Prior Publication Data

US 2021/0045260 A1 Feb. 11, 2021

Related U.S. Application Data

(62) Division of application No. 15/299,941, filed on Oct. 21, 2016, now Pat. No. 10,772,228.

(Continued)

(51) Int. Cl.
*H05K 5/06* (2006.01)
*A61J 1/00* (2023.01)
(Continued)

(52) U.S. Cl.
CPC ................ *H05K 5/069* (2013.01); *A61J 1/00* (2013.01); *A61N 1/3758* (2013.01); *A61N 1/378* (2013.01);
(Continued)

(58) Field of Classification Search
CPC .... H05K 5/069; H05K 5/0086; H05K 7/1417; A61J 1/00; A61N 1/378; H01M 2220/30; H01M 50/55; Y02E 60/10
See application file for complete search history.

(56) References Cited

U.S. PATENT DOCUMENTS

| 4,785,827 A | 11/1988 | Fischer |
| 5,276,354 A | 1/1994 | Link ..................... G11C 5/141 |
| | | 257/666 |

(Continued)

FOREIGN PATENT DOCUMENTS

| DE | 3041478 A1 | 6/1982 |
| EP | 1955732 A1 | 8/2008 |

(Continued)

OTHER PUBLICATIONS

Merriam-Webster OnLine definition of Transparent. No date.*

(Continued)

*Primary Examiner* — Nathan W Ha
(74) *Attorney, Agent, or Firm* — Mueting Raasch Group

(57) ABSTRACT

Various embodiments of a sealed package and method of forming such package are disclosed. The package can include a housing having an inner surface and an outer surface, and a substrate having a first major surface and a second major surface. The package can also include an electronic device disposed on the first major surface of the substrate, and a power source disposed at least partially within the housing. The substrate can be sealed to the housing such that a non-bonded electrical connection is formed between a device contact of the electronic device and a power source contact of the power source.

7 Claims, 8 Drawing Sheets

Related U.S. Application Data

(60) Provisional application No. 62/250,194, filed on Nov. 3, 2015.

(51) Int. Cl.

| | |
|---|---|
| *A61N 1/375* | (2006.01) |
| *A61N 1/378* | (2006.01) |
| *H05K 5/00* | (2006.01) |
| *H05K 7/14* | (2006.01) |
| *H01M 50/55* | (2021.01) |

(52) U.S. Cl.

CPC .......... *H05K 5/0086* (2013.01); *H05K 7/1417* (2013.01); *H01M 50/55* (2021.01); *H01M 2220/30* (2013.01)

(56) References Cited

U.S. PATENT DOCUMENTS

| | | | |
|---|---|---|---|
| 5,470,345 A | 11/1995 | Hassler et al. | |
| 5,814,091 A | 9/1998 | Dahlberg et al. | |
| 6,414,835 B1 | 7/2002 | Wolf .................... | A61N 1/3754 361/302 |
| 7,647,110 B2 | 1/2010 | Hörnfeldt et al. | |
| 7,794,866 B2 | 9/2010 | Youker et al. | |
| 7,822,482 B2 | 10/2010 | Gerber | |
| 8,231,998 B2 | 7/2012 | Sastry et al. | |
| 8,473,056 B2 | 6/2013 | Engmark et al. | |
| 8,626,310 B2* | 1/2014 | Barror .................... | H01Q 1/273 607/36 |
| 8,666,505 B2 | 3/2014 | O'Brien et al. | |
| 8,796,109 B2 | 8/2014 | Ruben et al. | |
| 10,098,589 B2* | 10/2018 | Ruben ................. | A61B 5/0245 |
| 10,772,228 B2* | 9/2020 | Day .................... | H05K 5/0086 |
| 2001/0039374 A1 | 11/2001 | Schulman .......... | A61B 5/14532 600/300 |
| 2002/0138114 A1 | 9/2002 | Gramse ................. | A61N 1/375 607/37 |
| 2003/0040781 A1 | 2/2003 | Larson .................... | A61N 1/375 607/36 |
| 2008/0188902 A1 | 8/2008 | Starke .................... | A61N 1/375 607/36 |
| 2009/0059468 A1 | 3/2009 | Iyer | |
| 2010/0308453 A1 | 12/2010 | Scheid ................ | H01L 23/3675 257/698 |
| 2012/0101540 A1 | 4/2012 | O'Brien et al. | |
| 2012/0225506 A1 | 9/2012 | Nguyen ........... | H01L 21/67005 438/26 |
| 2012/0300421 A1* | 11/2012 | Askarinya ......... | A61M 5/14276 29/829 |
| 2013/0196214 A1 | 8/2013 | Scott et al. | |
| 2016/0185081 A1 | 6/2016 | Sandlin et al. | |
| 2016/0190052 A1 | 6/2016 | Ruben et al. | |
| 2016/0192524 A1 | 6/2016 | Ruben | |
| 2017/0100597 A1* | 4/2017 | Barror ................ | A61N 1/37223 |

FOREIGN PATENT DOCUMENTS

| | | |
|---|---|---|
| WO | 2010000026 A1 | 1/2010 |
| WO | WO 2016/106269 A1 | 6/2016 |
| WO | WO 2016/106272 A1 | 6/2016 |
| WO | WO 2016/106274 A1 | 6/2016 |
| WO | WO 2016/106323 A1 | 6/2016 |

OTHER PUBLICATIONS

MerriamWebster OnLine Dictionary Definition of When. No Date.*
Chinese Office Action with translation from CN Application No. 201680064361.X dated Apr. 6, 2021, 16 pages.
U.S. Appl. No. 62/096,706, filed Dec. 24, 2014, Sandlin et al.
U.S. Appl. No. 14/949,277, filed Nov. 23, 2015, 30 pages.
(PCT/US2016/058966) PCT Notification of Transmittal of the International Search Report and the Written Opinion of the International Searching Authority, mailed Feb. 3, 2017, 9 pages.

* cited by examiner

502 — Dispose a Power Source within Cavity of Housing

504 — Dispose Electronic Device on Wafer

506 — Seal Wafer to Housing

508 — Remove Portion of Wafer

602 — Form Opening Through Welding Ring Wafer

604 — Dispose Electronic Device on Substrate Wafer

606 — Seal Substrate Wafer to Welding Ring Wafer

608 — Seal Power Source to Welding Ring Wafer

610 — Remove Portion of Welding Ring Wafer and Substrate Wafer

SEALED PACKAGE INCLUDING ELECTRONIC DEVICE AND POWER SOURCE

CROSS-REFERENCE TO RELATED APPLICATIONS

This application is a divisional of U.S. patent application Ser. No. 15/299,941, filed Oct. 21, 2016, which claims priority to U.S. Provisional Patent Application No. 62/250, 194, filed Nov. 3, 2015, which are incorporated herein by reference.

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators and drug pumps, which include electronic circuitry and one or more power sources, require an enclosure or housing to contain and seal these elements within a body of a patient. Many of these IMDs include one or more electrical feedthrough assemblies to provide electrical connections between the elements contained within the housing and components of the IMD external to the housing, for example, one or more sensors, electrodes, and lead wires mounted on an exterior surface of the housing, or electrical contacts housed within a connector header, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically-sealed housing to contain electronic circuitry of the sensor and an electrical feedthrough assembly to provide electrical connection between one or more lead wires, which extend within the implantable lead body, and the contained circuitry.

SUMMARY

In general, the present disclosure provides various embodiments of a sealed package and a method of forming such package. In one or more embodiments, the sealed package includes a housing having an inner surface and an outer surface, and a substrate that includes a first major surface and a second major surface. The package can also include an electronic device disposed on the first major surface of the substrate, where the device includes a device contact. The package can also include a power source disposed within the housing, where the power source includes a power source contact. In one or more embodiments, the substrate is hermetically sealed to the housing such that a non-bonded electrical connection is formed between the device contact and the power source contact.

In one aspect, the present disclosure provides a hermetically-sealed package that includes a housing having an inner surface and an outer surface, and a substrate that includes a first major surface and a second major surface. The package further includes an electronic device disposed on the first major surface of the substrate, where the device includes a device contact, and a power source disposed at least partially within the housing, where the power source includes a power source contact. The substrate is hermetically sealed to the housing such that a non-bonded electrical connection is formed between the device contact and the power source contact.

In another aspect, the present disclosure provides a method of forming a hermetically-sealed package. The method includes disposing a power source at least partially within a housing, disposing an electronic device on a major surface of a substrate, and hermetically sealing the substrate to the housing such that a non-bonded electrical connection is formed between a device contact of the electronic device and a power source contact of the power source. Hermetically sealing the substrate to the housing includes laser bonding the major surface of the substrate to the housing.

In another aspect, the present disclosure provides a method of forming a hermetically-sealed package that includes forming a recess in a major surface of a wafer, disposing a power source within the recess of the wafer, and disposing an electronic device on a major surface of a substrate. The method further includes hermetically sealing the major surface of the device substrate to the wafer such that a non-bonded electrical connection is formed between a device contact of the electronic device and a power source contact of the power source, and removing a portion of the wafer and substrate to form the hermetically-sealed package. In another aspect, the present disclosure provides a method of forming a hermetically-sealed package, including disposing a power source within a cavity of a housing, and disposing an electronic device on a major surface of a substrate wafer. The method further includes hermetically sealing the major surface of the substrate wafer to the housing such that the electronic device is disposed within the cavity of the housing and a non-bonded electrical connection is formed between a device contact of the electronic device and a power source contact of the power source. The method further includes removing a portion of the substrate wafer to form the hermetically-sealed package.

In another aspect, the present disclosure provides a method of forming a hermetically-sealed package. The method includes forming an opening through a welding ring wafer, disposing an electronic device on a major surface of a substrate, and hermetically sealing the major surface of the substrate to a first major surface of the welding ring wafer such that the electronic device is registered with the opening formed through the welding ring wafer. The method further includes hermetically sealing a housing of a power source to a second major surface of the welding ring wafer such that the power source is registered with the opening formed through the welding ring wafer, where a non-bonded electrical connection is formed between a device contact of the electronic device and a power source contact of the power source when the housing of the power source is hermetically sealed to the second major surface of the welding ring wafer. The method further includes removing a portion of the welding ring wafer and the substrate to form the hermetically-sealed package.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIG. 5 is a schematic exploded top perspective view of another embodiment of a sealed package.

FIG. 6 is a schematic exploded bottom perspective view of the sealed package of FIG. 5.

DETAILED DESCRIPTION

Figure 1:
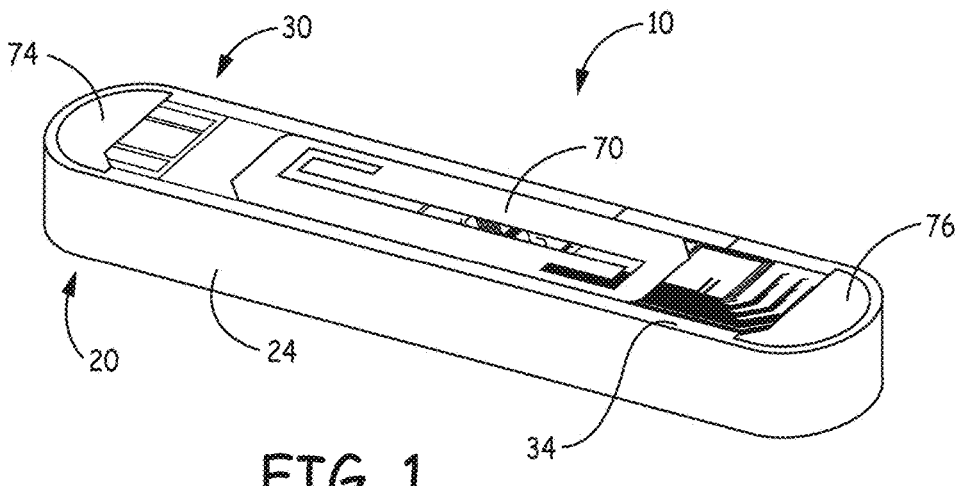
FIG. 1 is a schematic perspective view of one embodiment of a sealed package.

In general, the present disclosure provides various embodiments of a sealed package and a method of forming such package. In one or more embodiments, the sealed package includes a housing having an inner surface and an outer surface, and a substrate that includes a first major surface and a second major surface. The package can also include an electronic device disposed on the first major surface of the substrate, where the device includes a device contact. The package can also include a power source disposed within the housing, where the power source includes a power source contact. In one or more embodiments, the substrate is sealed to the housing such that a non-bonded electrical connection is formed between the device contact and the power source contact. Further, in one or more embodiments, the substrate can be hermetically sealed to the housing using any suitable technique or combination of techniques.

Any suitable technique or combination of techniques can be utilized to seal the substrate to the housing. For example, the housing can include a flange that is adapted to seal the housing to the substrate. In one or more embodiments, such flange can be integral with the housing. As used herein, the term "integral" means that two or more elements are manufactured together at the same time, that is, made together as one part and not two or more separately manufactured parts that are subsequently joined together. In one or more embodiments, the flange can be integral with the substrate and sealed to the housing using any suitable technique or combination of techniques. In one or more embodiments, the flange can be a separate part or component, e.g., a welding ring, that is sealed to the substrate and the housing.

Further, the power source can include a casing or container such that the housing of the package is provided by the power source. In one or more embodiments, the package can include a separate housing within which the power source and power source casing can be disposed. In one or more embodiments, the power source does not include a casing such that active material and components of the power source are disposed directly within the housing, and a cover or wall can be disposed over the power source to seal it within the housing.

The various embodiments of sealed packages described herein can include or be utilized with any device or system that requires sealed conductive pathways. For example, one or more embodiments of sealed packages described herein can include an implantable medical device or system disposed within the sealed package. In one or more embodiments, the sealed package can be electrically connected to an implantable medical device. Nearly any implantable medical device or system employing leads may be used in conjunction with the various embodiments of sealed packages described herein. Representative examples of implantable medical devices included in or utilized with the various embodiments of sealed packages described herein include hearing implants, e.g., cochlear implants; sensing or monitoring devices; signal generators such as cardiac pacemakers or defibrillators;

neurostimulators (such as spinal cord stimulators, brain or deep brain stimulators, peripheral nerve stimulators, vagal nerve stimulators, occipital nerve stimulators, subcutaneous stimulators, etc.); gastric stimulators; or the like.

Figure 2:
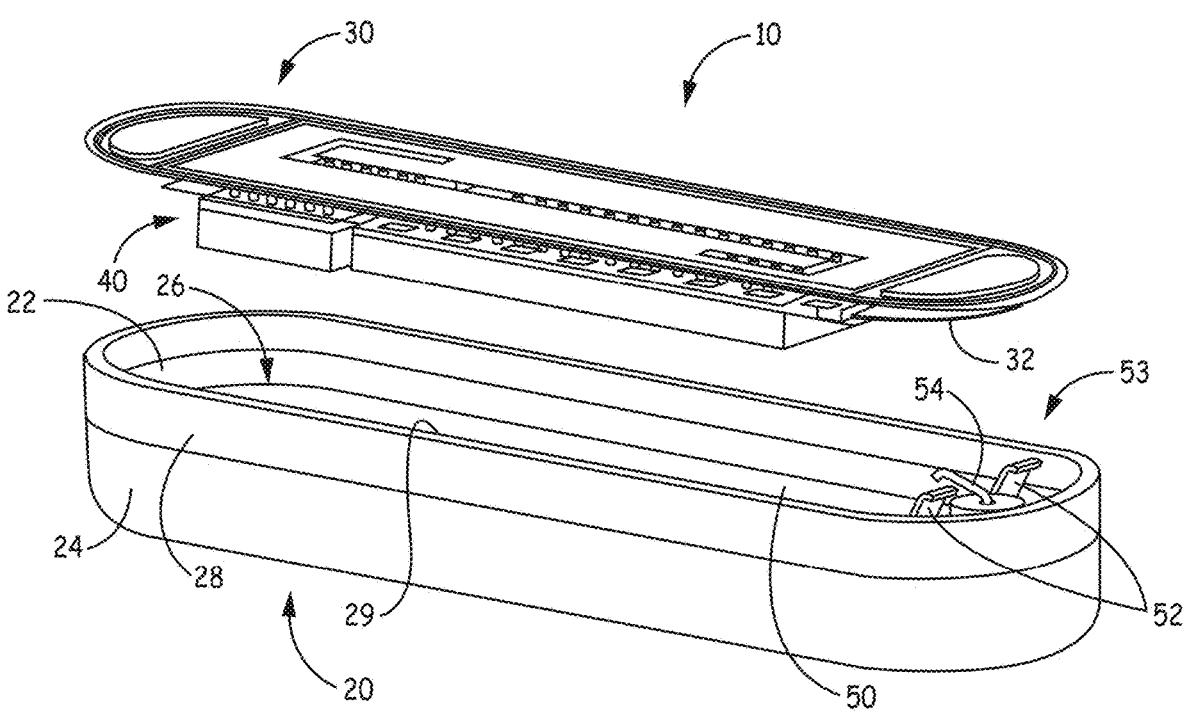
FIG. 2 is a schematic exploded view of the sealed package of FIG. 1.
Figure 3:
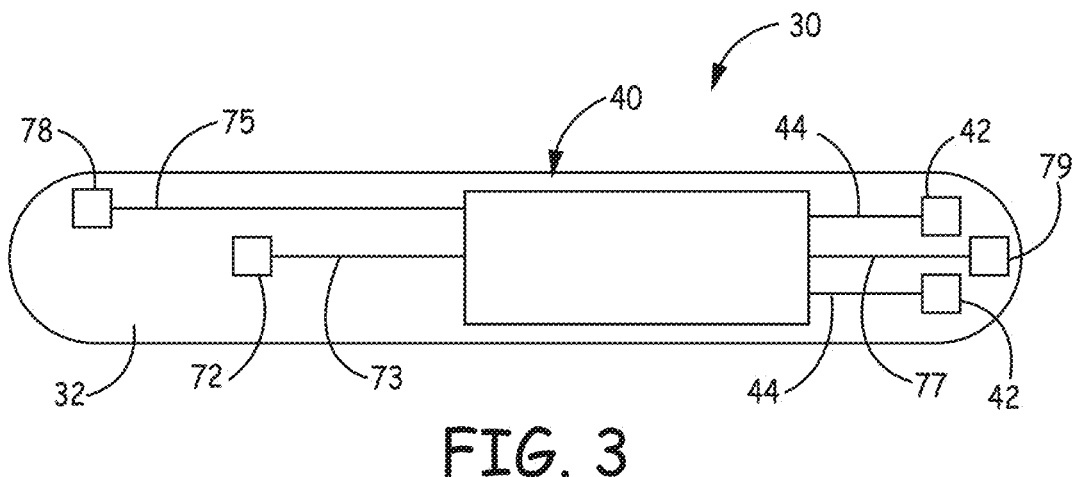
FIG. 3 is a schematic plan view of a first major surface of a substrate of the sealed package of FIG. 1.
Figure 4:
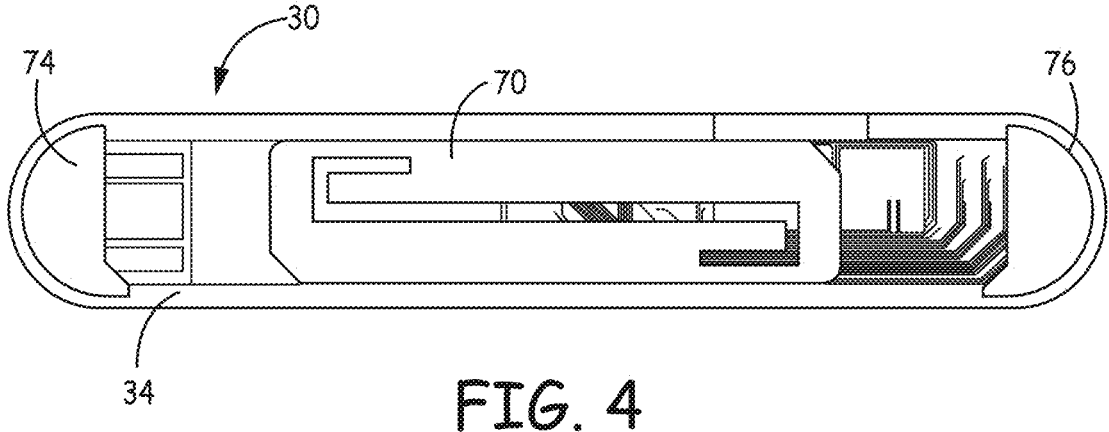
FIG. 4 is a schematic plan view of a second major surface of the substrate of the sealed package of FIG. 1.

FIGS. 1-4 are various schematic views of one embodiment of a sealed package 10. The package 10 includes a housing 20 and a substrate 30. The housing 20 includes an inner surface 22 and an outer surface 24. Further, the substrate 30 includes a first major surface 32 and a second major surface 34. The package 10 also includes one or more electronic devices 40 disposed on the first major surface 32 of the substrate 30. The electronic device 40 can include one or more device contacts 42 (FIG. 3). The package 10 also includes a power source 50 that is disposed at least partially within the housing 20. In one or more embodiments, the power source 50 can be disposed within a cavity 26 of the housing 20. The power source 50 includes one or more power source contacts 52, 54 as is further described herein.

The substrate 30 can be sealed to the housing 20. In one or more embodiments, the substrate 30 can be hermetically sealed to the housing 20. Further, in one or more embodiments, the substrate 30 can be sealed to the housing 20 such that a non-bonded electrical connection can be formed between one or more device contacts 42 and one or more power source contacts 52, 54.

The housing 20 can include any suitable material or combination of materials, e.g., metallic, polymeric, ceramic, or inorganic materials. In one or more embodiments, the housing 20 can include at least one of glass, quartz, silica, sapphire, silicon carbide, diamond, MP35N (available from Elgiloy Specialty Metals, Sycamore, IL), and gallium nitride. In one or more embodiments, the housing 20 can include at least one of copper, silver, titanium, niobium, zirconium, tantalum, stainless steel, platinum, and iridium. In one or more embodiments, the housing 20 can include the same material or combination of materials as the substrate 30. Further, in one or more embodiments, the housing 20 can include biocompatible materials such that the package 10 can be implanted within a patient's body. Further, one or more coatings or layers can be disposed on the outer surface 24 of the housing that provide biocompatibility. In one or more embodiments, the housing 20 can be electrically conductive to provide a ground electrode for the package 10 as is known in the art. In one or more embodiments, the housing 20 can be nonconductive.

Further, the housing 20 can take any suitable shape or combination of shapes and can have any suitable dimensions. In one or more embodiments, the housing 20 takes a shape that forms the cavity 26 that can accommodate the power source 50 (including active material and power source electronics) and electronic device 40 as is further described herein.

Sealed to the housing 20 is the substrate 30. In one or more embodiments, the substrate 30 can be a non-conductive or insulative substrate such that the electronic device 40, external electrodes 74, 76, and any conductors or other devices disposed on the substrate can be electrically isolated if desired. The substrate 30 can include any suitable material or combination of materials. In one or more embodiments, the substrate 30 can include at least one of glass, quartz, silica, sapphire, silicon carbide, diamond, and gallium nitride, or any combinations thereof. In one or more embodiments, the substrate 30 can include the same material or materials as the housing 20. As with the housing 20, the substrate 30 can include a biocompatible material. Further, the substrate 30 can include one or more coatings or layers that can provide biocompatibility.

Further, the substrate 30 can be a transparent substrate. As used herein, the phrase "transparent substrate" refers to a substrate that can transmit a given percentage of light incident thereon during use of laser bonding techniques described herein to preferentially heat only an outer surface of the substrate (e.g., first major surface 32 or second major surface 34 of substrate 30), and not an inner bulk of the substrate, and thereby create a bond that has a relatively greater strength than the bulk strength of the substrate. In one or more embodiments, the substrate 30 can be substantially transparent at a desired wavelength or range of wavelengths. As used herein, the phrase "substantially transparent" means that the substrate transmits greater than 50% of light incident on the substrate for a selected wavelength or range of wavelengths, assuming no reflection at the air-substrate boundaries. In one or more embodiments, the substrate 30 can be substantially transmissive to light having a wavelength of at least 200 nm. In one or more embodiments, the substrate 30 can be substantially transmissive to light having a wavelength of greater than 10,000 nm. In one or more embodiments, the substrate 30 can be substantially transmissive to light having a wavelength in a range of 200 nm to 10,000 nm. In one or more embodiments, the substrate 30 can be substantially transmissive to at least one of UV light, visible light, and IR light.

The substrate 30 can include any suitable dimensions, e.g., thicknesses. Further, the substrate 30 can take any suitable shape or combinations of shapes. In one or more embodiments, the substrate 30 can take a shape or combination of shapes that is complementary to a shape of the housing 20 such that the substrate can be sealed to the housing and provide a low-profile shape for the sealed package 10. Further, the substrate 30 can be a single, unitary substrate or multiple substrates joined together.

Disposed on the first major surface 32 of the substrate 30 is the electronic device 40. Although depicted as being disposed on the first major surface 32, the electronic device 40 can be disposed on the second major surface 34, or electronic devices can be disposed on both the first and second major surfaces. In one or more embodiments, one or more electronic devices can be disposed within the housing 20 and not attached to the substrate 30. Any suitable electronic device 40 or devices can be disposed on the first major surface 32, e.g., capacitors, transistors, integrated circuits, including controllers and multiplexers, sensors, etc.

Further, any suitable number of electronic devices 40 can be disposed on the first major surface 32. Further, any suitable technique or combination of techniques can be utilized to dispose the electronic device 40 on the first major surface 32. In one or more embodiments, the electronic device 40 can be formed on the first major surface 32 of the substrate 30. In one or more embodiments, the device 40 can be formed separately and then attached to the first major surface 32. Any suitable technique or combination of techniques can be utilized to attach the electronic device 40 to the substrate 30, e.g., a bond can be formed between the electronic device and the first major surface 32 of the substrate.

As mentioned herein, the electronic device 40 can include one or more sensors, e.g., one or more optical sensors. In one or more embodiments, at least a portion of the substrate 30 can be transparent such that an optical sensor disposed on the first major surface 32 can detect one or more external signals, e.g., from a patient, when the package 10 is disposed within the patient. In one or more embodiments, the at least a portion of the substrate 30 can be transparent enough to enable transmission of all, or a sufficient magnitude, of the light that is incident on the substrate for reception by the optical sensor such that the received light can be processed to detect the external signal. For example, the electronic device 40 can include an infrared or near-infrared oxygen sensor that can detect through the substrate 30 the oxygen level of the blood of the patient.

The electronic device 40 can be electrically connected to one or more additional electronic devices disposed on one or both of the first major surface 32 and second major surface 34, or within the housing 20. For example, the electronic device 40 can be electrically connected to the power source 50 using any suitable technique or combination of techniques. In one or more embodiments, the electronic device 40 can include one or more device contacts 42 that are electrically connected to the electronic device using any suitable technique or combination of techniques. For example, FIG. 3 is a schematic plan view of the first major surface 32 of the substrate 30. Device contacts 42 are electrically connected to device 40 through conductors 44. Although illustrated as including two device contacts 42, the package 10 can include any suitable number of device contacts. The device contacts 42 can include any suitable contacts, pads, terminals, etc., that provide electrical connection to other devices, e.g., power source 50. The contacts 42 can take any suitable shape or combination of shapes and be disposed in any suitable location on or in the first major surface 32 of the substrate 30. Any suitable technique or combination of techniques can be utilized to form device contacts 42 and conductors 44, e.g., chemical vapor deposition, plasma vapor deposition, physical vapor deposition, etc., followed by photolithography, chemical etching, etc. Further, the device contacts 42 and conductors 44 can include any suitable conductive material or combination of conductive materials. In one or more embodiments, the electronic device 40 can be electrically connected to other electronic circuitry or devices disposed on or adjacent the substrate 30 or within the housing 20.

The electronic device 40 can be electrically connected to device contacts 42 using any suitable technique or combination of techniques. For example, in one or more embodiments, solder bumps and/or contact pads of the electronic device 40 can be directly attached to one or more contacts 42 using any suitable technique or combination of techniques, e.g., soldering, welding, laser bonding, mechanically connecting (e.g., direct-pressure contacts), etc. In one or more embodiments, one or more conductors 44 can be electrically connected to one or more device contacts 42 and one or more solder bumps and/or contact pads of the electronic device 40 using any suitable technique or combination of techniques, e.g., soldering, welding, laser bonding, mechanically connecting (e.g., direct-pressure contacts), etc.

Any suitable technique or combination of techniques can be utilized to dispose the device contacts 42 and the conductors 44 on the substrate 30, e.g., the techniques described in U.S. Patent Application No. 62/096,706, entitled KINETICALLY LIMITED NANO-SCALE DIFFUSION BOND STRUCTURES AND METHODS. For example, electromagnetic radiation can be directed through substrate 30 from the second major surface 34 to a region between the device contacts 42, the conductors 44, and the substrate 30. The electromagnetic radiation can form a bond that seals the device contacts 42 and the conductors 44 to the substrate 30 in any suitable pattern or shape. The bond can be a laser bond.

The package 10 can also include power source 50. Any suitable power source or combination of power sources can be utilized with package 10, e.g., one or more batteries, capacitors, inductive-coupled energy devices, photovoltaic devices, betavoltaic devices, alphavoltaic devices, and thermo-electric devices.

The power source 50 can be disposed in any suitable location. In one or more embodiments, the power source 50 is disposed at least partially within the housing 20. As used herein, the term "at least partially within" means that at least a portion of the power source 50 is disposed within the housing 20. In one or more embodiments, the entire power source 50 can be disposed within the housing 20. As is further described herein, the power source 50 can include its own housing or casing. In one or more embodiments, the housing 20 provides at least a portion of an outer casing for the power source. For example, the inner surface 22 of the housing 20 can provide a portion of a casing of the power source 50, and a separate cover or protective layer can be disposed within the housing such that the power source is between the protective layer and the inner surface of the housing. The power source 50 can be integral with the housing 20. In one or more embodiments, the power source 50 is a separate element that is separately manufactured and then disposed within the housing 20.

The power source 50 includes one or more power source contacts 52, 54. Although depicted as including three contacts 52, 54 the power source 50 can include any suitable number of contacts that can be electrically connected to one or more devices to provide electrical energy to such devices from the power source. The power source contacts 52, 54 can be disposed in any suitable location relative to the power source 50. As illustrated in FIG. 2, the power source contacts 52, 54 are disposed at a first end 53 of the power source 50.

The power source contacts 52, 54 can include any suitable contact, e.g., the same contacts described regarding device contacts 42. In one or more embodiments, the power source contacts 52, 54 can include one or more compressible or resilient members that can engage one or more device contacts, e.g., device contacts 42, when the substrate 30 is sealed to the housing 20. Each power source contact 52 can be the same contact or type of contact. In one or more embodiments, each power source contact 52 can be different from each additional power source contact. For example, as illustrated in FIG. 2, the power source 50 includes an additional power source contact 54 that can be the same as or different from the power source contacts 52.

The electronic device 40 can, in one or more embodiments, be electrically connected to the power source 50 using any suitable technique or combination of techniques. In one or more embodiments, the electronic device 40 can be electrically connected to the power source 50 when the substrate 30 is sealed to the housing 20. Any suitable technique or combination of techniques can be utilized to electrically connect the electronic device 40 to the power source 50 when the substrate 30 is sealed to the housing 20. For example, one or more power source contacts 52, 54 can be electrically connected to one or more device contacts 42 when the substrate 30 is sealed to the housing 20. Any suitable electrical coupling between the power source contacts 52, 54 and the device contacts 42 can be utilized. In one or more embodiments, a non-bonded electrical connection can be formed between one or more device contacts 42 and one or more power source contacts 52, 54 when the substrate 30 is sealed to the housing 20. As used herein, the term "non-bonded electrical connection" means that an electrical connection is formed between two or more contacts, terminals, electrodes, etc., that can be maintained by suitable contact pressure between the two or more contacts to maintain the electrical connection, without the use of a bonding agent, e.g., a conductive adhesive, solder, etc. In one or more embodiments, this non-bonded electrical connection can be formed between one or more device contacts 42 and one or more power source contacts 52, 54 by mechanical engagement between such contacts using any suitable connecting element or elements, e.g., pin and sleeve connecting elements. In one or more embodiments, at least one of the device contacts 42 and the power source contacts 52, 54 can include a compressible or resilient member that mechanically engages another contact when the substrate 30 is sealed to the housing 20. In one or more embodiments, a bonded electrical connection can be provided between the one or more power source contacts 52, 54 and the one or more device contacts 42 using any suitable technique, e.g., welding, adhering using a conductive adhesive (e.g., UV or thermally curable adhesives), soldering, laser bonding, etc.

The substrate 30 can be sealed to the housing 20 using any suitable technique or combination of techniques, e.g., mechanically fastening, adhering, press fitting, laser bonding, magnetic coupling, etc. In one or more embodiments, the first major surface 32 of the substrate 30 can be sealed to an edge surface 29 of a flange 28. The flange 28 can be integral with the housing 20. In one or more embodiments, the flange 28 can be attached to the housing using any suitable technique or combination of techniques.

In one or more embodiments, the substrate 30 can be hermetically sealed to the housing 20. Any suitable technique or combination of techniques can be utilized to hermetically seal the substrate 30 to the housing 20. For example, in one or more embodiments, the substrate 30 can be hermetically sealed to the housing 20 by a bond. Any suitable technique or combination of techniques can be utilized to form such bond, e.g., the techniques described in co-owned and co-filed U.S. Patent Application No. 62/096,706, entitled KINETICALLY LIMITED NANO-SCALE DIFFUSION BOND STRUCTURES AND METHODS. In one or more embodiments, electromagnetic radiation (e.g., light) can be directed through substrate 30 from the second major surface 34 and focused at a region between the substrate and the housing 20. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 2000 nm. For example, laser light can include UV light, visible light, IR light, and combinations thereof. The UV light can be provided by a UV laser that has any suitable wavelength or range of wavelengths and any suitable pulse width. In one or more embodiments, a UV laser can be utilized to provide light having a wavelength in a range of 100-400 nm and a pulse width in a range of 1-100 ns. In one or more embodiments, the materials for the substrate 30 and the housing 20, and the power level and wavelength of the light used may be selected such that the light may not directly damage, ablate, warp, or cut the substrate and the housing, and such that the substrate and the housing retain their bulk properties.

In general, light can be provided by any suitable laser or laser system. For example, the laser may generate light having a relatively narrow set of wavelengths (e.g., a single wavelength). In one or more embodiments, the light emitted by the laser may form a collimated beam that may not be focused at a particular point. In one or more embodiments, the light emitted by the laser may be focused at a focal point at a region between the first major surface 32 of the substrate 30 and the housing 20 to generate a laser bond. Although the laser may provide light that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat, Gaussian, or other suitable spatial energy profile.

As mentioned herein, one or more electronic devices 40 can be disposed on the first major surface 32 of the substrate 30. In one or more embodiments, one or more additional devices or features can also be disposed on the second major surface 34 of the substrate 30. For example, in the embodiment illustrated in FIGS. 1-4, the first electrode 74 and the second electrode 76 are disposed on the second major surface 34 of the substrate 30. The first and second electrodes 74, 76 can include any suitable electrode or combination of electrodes and can take any suitable shape and have any suitable dimensions.

One or both of the first and second electrodes 74, 76 can be utilized to electrically connect the package 10 to any suitable device or devices that are external to the package. For example, one or both of the first and second electrodes 74, 76 can electrically connect the package 10 to a lead of an implantable medical device. In one or more embodiments, one or both of the first and second electrodes 74, 76 can electrically connect the package 10 to one or more additional power sources. Further, in one or more embodiments, one or both of the first and second electrodes 74, 76 can be therapeutic electrodes that can be utilized for delivering and/or receiving one or more electrical signals to or from a patient, either while the package is external or internal to a patient. Any suitable technique or combination of techniques can be utilized to electrically connect the package 10 to one or more devices through one or both of the first electrode 74 and second electrode 76, e.g., soldering, physical contact, welding, etc. The first and second electrodes 74, 76 can include any suitable conductive material or combination of conductive materials, e.g., copper, silver, titanium, niobium, zirconium, tantalum, stainless steel, platinum, iridium, or combinations thereof. In one or more embodiments, the first and second electrodes 74, 76 can include two or more materials, e.g., bi-metals, clad laminates, etc.

Further, the first and second electrodes 74, 76 can take any suitable shape or combination of shapes. In one or more embodiments, the first and second electrodes 74, 76 can take a circular shape in a plane parallel to the second major surface 34 of the substrate 30. In one or more embodiments, the first and second electrodes 74, 76 can take a rectangular shape in the plane parallel to the second major surface 34. Further, the first and second electrodes 74, 76 can take any suitable shape or combination of shapes in a plane orthogonal to the second major surface 34, e.g., square, tapered, domed, etc. In one or more embodiments, the first and second electrodes 74, 76 can include complex shapes such as grooves or channels formed in the electrode to facilitate attachment of conductors or electronic devices to the contacts.

The first and second electrodes 74, 76 can also include any suitable dimensions. In one or more embodiments, the first and second electrodes 74, 76 can have any suitable thickness in a direction normal to the second major surface 34 of the substrate 30. In one or more embodiments, this thickness can be at least 10 micrometers. In one or more embodiments, the thickness can be no greater 200 micrometers. In one or more embodiments, the first and second electrodes 74, 76 can be of sufficient size and thickness to enable laser, resistance, or other welding and joining techniques to be utilized to electrically couple conductors and/or electronic devices to the electrode.

The first and second electrodes 74, 76 can be electrically connected to one or more electronic devices disposed on or within the package, e.g., electronic device 40. Any suitable technique or combination of techniques can be utilized to electrically connect one or both of the first and second electrodes 74, 76 to one or more devices disposed on or within the housing. In one or more embodiments, the first electrode 74 can be electrically connected to device 40 through via 78 (FIG. 3), which is electrically connected to device 40 through conductor 75. Via 78 can be formed between the first major surface 32 and the second major surface 34 of the substrate 30, and a conductive material can be disposed within the via using any suitable technique or combination of techniques. Similarly, second electrode 76 can be electrically connected to electronic device 40 through via 79 (FIG. 3), which is electrically connected to the device through conductor 77. Once again, via 79 can be formed between the first major surface 32 and the second major surface 34 of substrate 30, and conductive material can be disposed within the via using any suitable technique or combination of techniques.

The package 10 of FIGS. 1-4 can also include a conductor 70 disposed on the second major surface 34 of the substrate 30 or within the substrate between the first major surface 32 and the second major surface 34. The conductor 70 can include any suitable shape or combination of shapes and can be formed using any suitable conductive material. Although depicted as including one conductor 70, two or more conductors can be formed on the second major surface 34 of the substrate 30 or within the substrate. Further, the conductor 70 can be patterned to include any suitable shape or combination of shapes.

In one or more embodiments, the conductor 70 can be formed to provide an antenna, and the package 10 can be wirelessly coupled to a device or system through such antenna. Further, in one more embodiments, the conductor 70 can form an inductive coil that can be utilized to provide inductive coupling to one or more external devices, e.g., one or more inductive power sources.

The conductor 70 can be electrically connected to one or more electronic devices disposed within the housing of the package 10 using any suitable technique or combination of techniques. For example, a via 72 (FIG. 3) can be formed between the first major surface 32 and the second major surface 34 of the substrate 30 that is that is electrically connected to, e.g., electronic device 40 through conductor 73. Conductive material can be disposed within via 72 that electrically connects the conductor 72 electronic device 40. The conductor 70 can be electrically connected to the via 72 using any suitable technique or combination of techniques.

Figures 5, 6:
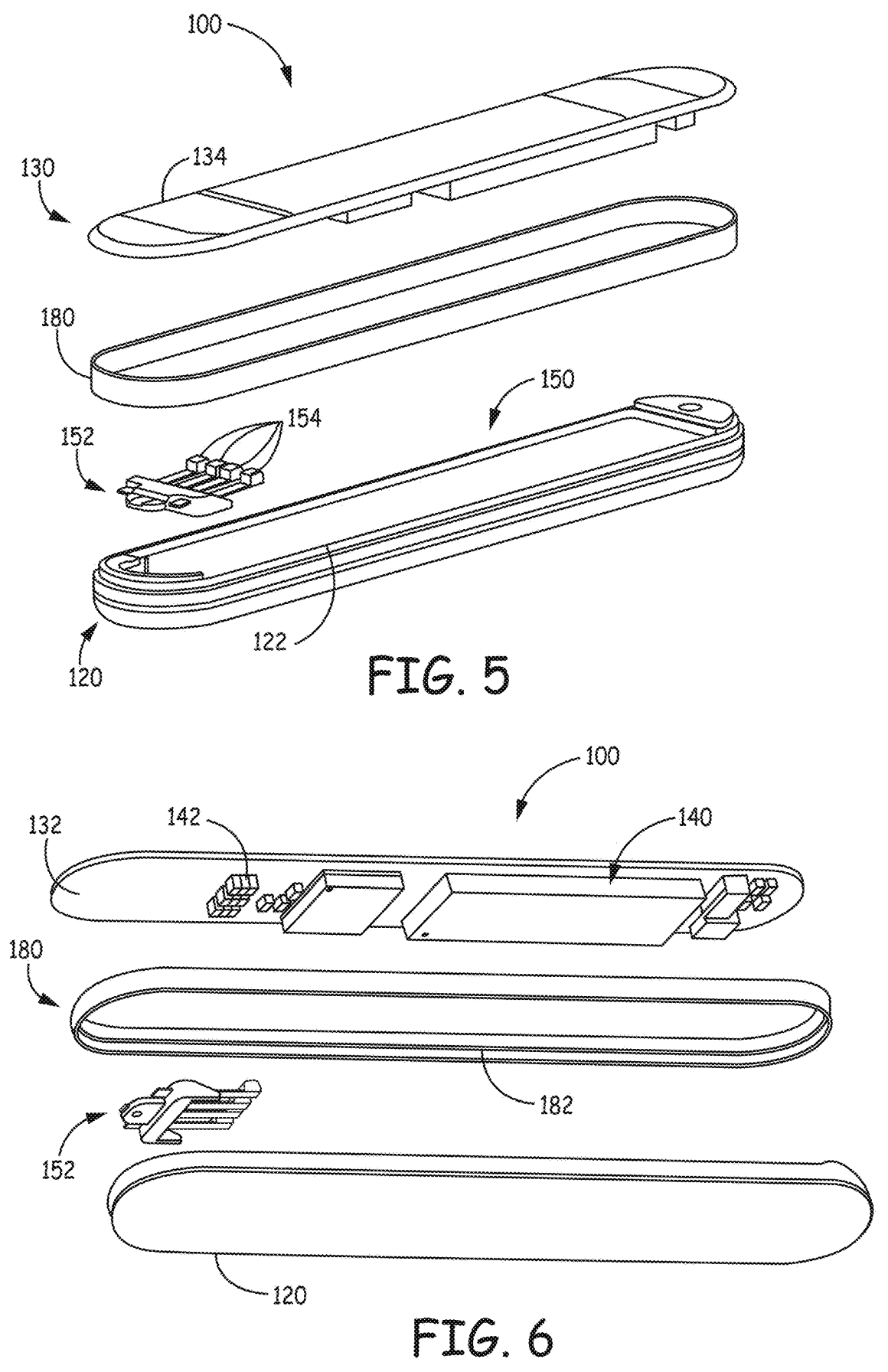

In general, the substrate 30 of package 10 can be sealed to housing 20 using any suitable technique or combination of techniques. For example, FIGS. 5-6 are schematic exploded views of another embodiment of a package 100. The package 100 includes a housing 120, a substrate 130 having a first major surface 132 and a second major surface 134, one or more electronic devices 140 disposed on the first major surface 132 of the substrate, and a power source 150 disposed at least partially within the housing. The electronic device 140 includes a device contact 142. Further, the power source 150 includes a power source contact 152. All of the design considerations and possibilities regarding the package 10 of FIGS. 1-4 apply equally to the package 100 of FIGS. 5-6.

One difference between package 100 of FIGS. 5-6 and package 10 of FIGS. 1-4 is that the substrate 130 is sealed to the housing 120 using a welding ring 180. The welding ring 180 can include any suitable material or combination materials, e.g., copper, silver, titanium, niobium, zirconium, tantalum, stainless steel, platinum, iridium, or combinations thereof. In one or more embodiments, the welding ring 180 can include two or more materials, e.g., bi-metals, clad laminates, etc. In one or more embodiments, the welding ring 180 can include any suitable bio-compatible and weldable materials. Further, the welding ring 180 can take any suitable shape and have any suitable dimensions. The welding ring 180 can be disposed between the first major surface 132 of the substrate 130 and the housing 120. In one or more embodiments, the welding ring 180 can be hermetically sealed to one or both of the first major surface 132 of the substrate 130 and the housing 120. The welding ring 180 can be sealed to one or both of the substrate 130 and the housing 120 using any suitable technique or combination of techniques, e.g., laser bonding. In one or more embodiments, the welding ring 180 is first attached to the second major surface 132 of the substrate 130 and then attached to the housing 120. In one or more embodiments, the welding ring 180 is first attached to the housing 120 and then to the first major surface 132 of the substrate 130.

In one or more embodiments, the welding ring 180 can include a flange or recessed portion 182 that is adapted to mate with a flange or recessed portion 122 of housing 120. The recessed portion 182 and the recessed portion 122 can provide additional surface area for sealing the welding ring

180 to the housing 120. Although not shown, the welding ring 180 can include a second recessed portion that is adapted to mate with a recessed portion formed in the substrate 130 (also not shown).

In the embodiment illustrated in FIGS. 5-6, power source contacts 152 include one or more deflectable tabs 154. The one or more deflectable tabs 154 electrically connect the power source 150 to the electronic device 140. In one or more embodiments, a non-bonded electrical connection can be formed between one or more device contacts 142 and the deflectable tabs 154 of power source contacts 152 when the substrate 130 is sealed to the housing 120.

Figure 7:
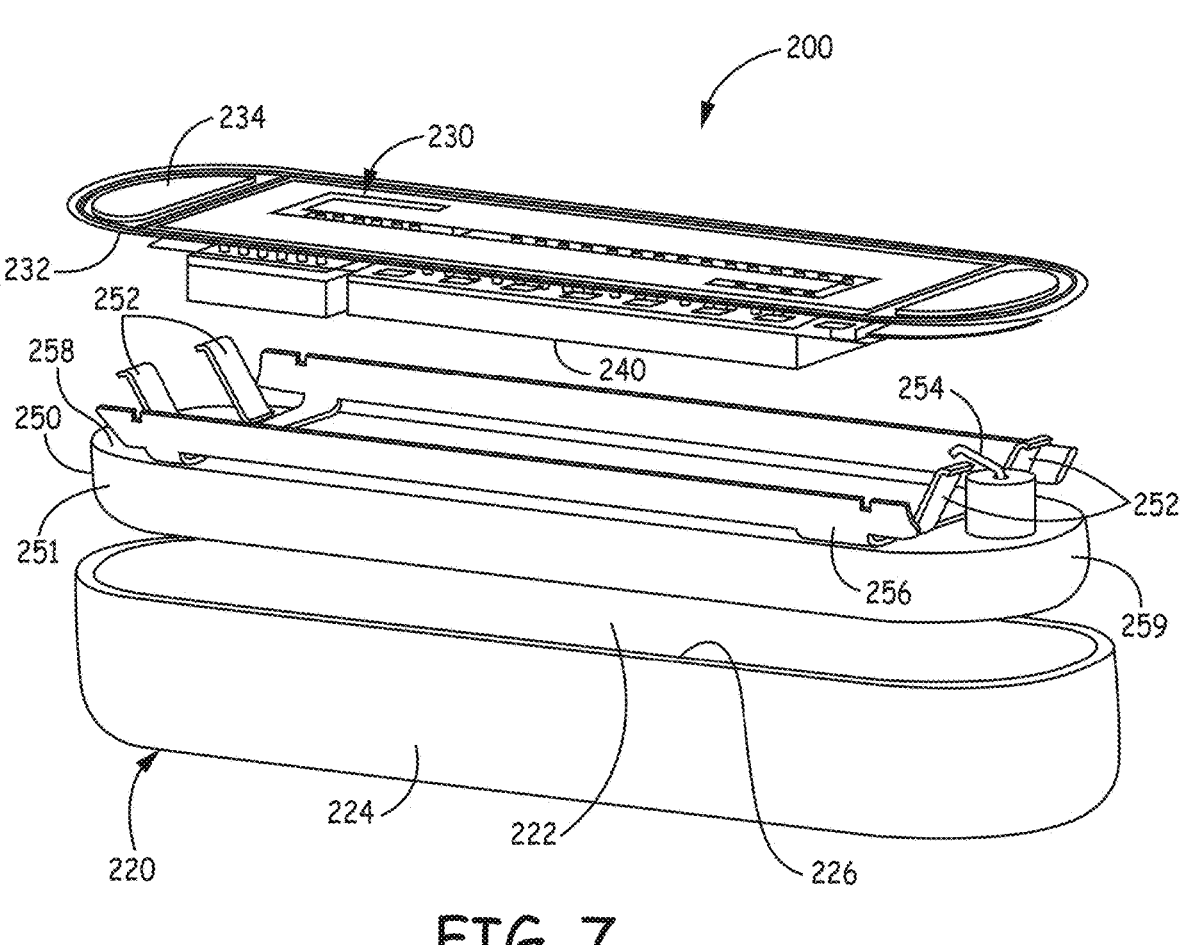
FIG. 7 is a schematic exploded view of another embodiment of a sealed package.

The housing of the various embodiments of packages described herein can be provided by the power source casing such that the package includes a single housing. In one or more embodiments, the housing can be a separate housing within which a power source including a power source casing can be disposed. For example, FIG. 7 is a schematic exploded view of another embodiment of a package 200. The package 200 includes a housing 220 that includes an inner surface 222 and an outer surface 224, a substrate 230 that includes a first major surface 232 and a second major surface 234, and an electronic device 240 disposed on the first major surface 232 of the substrate. The package 200 also includes a power source 250 that can be disposed at least partially within the housing 220. The electronic device 240 can include one or more device contacts (not shown), and the power source 250 can include one or more power source contacts 252, 254. The power source 250 includes a casing 251 that encloses one or more components of the source, e.g., active material such as a liquid or solid electrolyte and power source electronics. All of the design considerations and possibilities regarding the package 10 of FIGS. 1-4 and the package 100 of FIGS. 5-6 apply equally to the package 200 of FIG. 7.

One difference between the package 200 and package 10 is that the power source 250 includes a retaining member 256 that is adapted to be in contact with the inner surface 222 of the housing 220 when the power source 250 is disposed at least partially within the housing in cavity 226. In one or more embodiments, the retaining member 256 can provide a friction-fit between the power source 250 and the interior surface 222 of the housing 220. In one or more embodiments, the retaining member 256 can stabilize the power source 250 relative to the inner surface 222 of the housing 220. In one or more embodiments, the retaining member 256 can be electrically connected to the power source 250 and provide an electrical connection to the housing 220, e.g., the retaining member can provide ground from the power source to the housing.

The retaining member 256 can take any suitable shape or combination of shapes. Further, the retaining member 256 can include any suitable material or combination materials. In one or more embodiments, the retaining member 256 can include a resilient or compressible material that engages the inner surface 222 of the housing 220 when the power source 250 is disposed at least partially within the housing. For example, in one or more embodiments, the retaining member 256 can include a spring plate attached to or disposed on the casing 251 (or integral with the casing) of the power source 250 that is deflected when the power source is disposed at least partially within the housing 220. In such embodiments, the spring plate 256 provides a friction-fit with the inner surface 222 of the housing 220 and stabilizes the power source 250 relative to the housing.

Another difference between the package 200 and package 10 is that the power source 250 includes power source contacts 252 at both a first end 258 and a second end 259 of the power source. The power source contacts 252 can be disposed in any suitable location relative to the power source 250. Further, in the illustrated embodiment, the power source 250 includes an additional contact 254. The additional contact 254 can be disposed in any suitable location on or within the power source 250. Although depicted as including five power source contacts 252, 254, the power source 250 can include any suitable number of power source contacts that are adapted to electrically connect the power source to one or more electronic devices 240 or other components disposed within the housing 220 or external to the housing. In one or more embodiments, a non-bonded electrical connection can be formed between one or more device contacts (not shown) of the electronic device 240 and one or more of the power source contacts 252, 254 when the substrate 230 is sealed to the housing 220.

Figure 8:
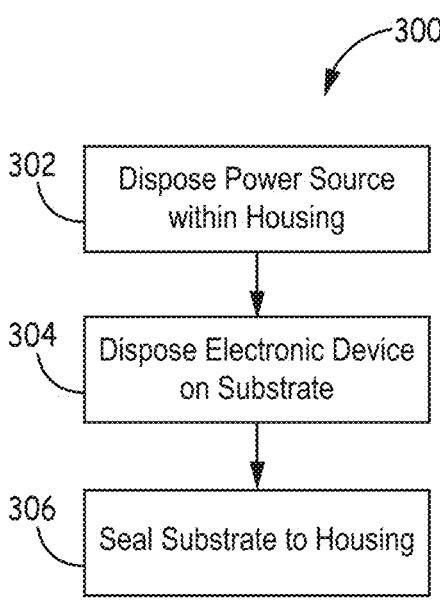
FIG. 8 is a flow chart of one embodiment of a method of forming a sealed package.

The various sealed packages of the present disclosure can be formed using any suitable technique or combination of techniques. For example, FIG. 8 is a flowchart of one method 300 for forming a sealed package. Although method 300 can be utilized to form any sealed package, the method will be described in reference to package 10 of FIGS. 1-4. The method 300 includes disposing the power source 50 within the housing 20 at 302 using any suitable technique or combination of techniques. One or more electronic devices 40 can be disposed on the substrate 30, e.g., on the first major surface 32 of the substrate 30, at 304, using any suitable technique or combination of techniques. For example, the electronic device 40 can be formed separately from the substrate 30 and then attached to the substrate, e.g., by soldering or welding the device to the substrate. The substrate 30 can be sealed to the housing 20 at 306 using any suitable technique or combination of techniques, e.g., either the first or second major surface 32, 34 of the substrate can be laser bonded to the housing 20. In one or more embodiments, the substrate 30 can be hermetically sealed to the housing 20. Further, in one or more embodiments, the substrate 30 can be sealed to the housing 20 such that a non-bonded electrical connection can be formed between one or more of the device contacts 42 and one or more of the power source contacts 52, 54. In one or more embodiments, one or more additional devices or elements (e.g., conductor 70, electrodes 74, 76) can be disposed on the second major surface 34 of the substrate 30 either before or after the substrate is sealed to the housing 20 using any suitable technique or combination of techniques.

Figure 9:
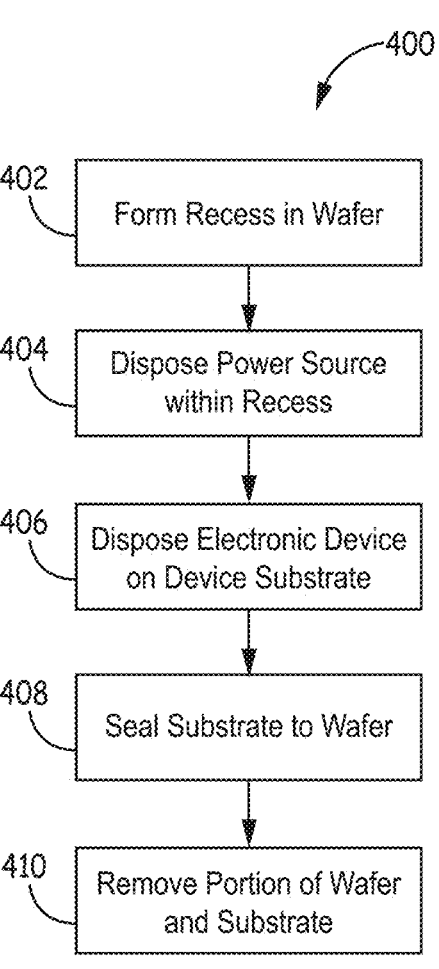
FIG. 9 is a flow chart of another embodiment of a method of forming a sealed package.

Further, for example, FIG. 9 is a flow chart of another embodiment of a method 400 for forming a sealed package, e.g., package 200 of FIG. 7. A housing wafer can be provided, and one or more recesses can be formed in the wafer at 402. The housing wafer can include any suitable material or combination of materials, e.g., the same materials described regarding housing 220 of FIG. 7. One or more power sources 250 can each be disposed within one or more of the recesses formed in the wafer at 404 using any suitable technique or techniques. In one or more embodiments, the power source 250 can be formed separately and then disposed within the recess. In one or more embodiments, the power source 250 can be formed within the recess using any suitable technique.

Further, at 406, one or more electronic devices 240 can be disposed on a major surface of the substrate 230, e.g., on the first major surface 232 of the substrate. In one or more embodiments, a plurality of devices can be disposed on a substrate wafer that are registered or aligned with the power sources 250 and the recesses. At 408, the major surface of the substrate 230 can be sealed to the wafer using any suitable technique or combination of techniques, e.g., the substrate can be sealed to the wafer using laser bonding. In one or more embodiments, a non-bonded electrical connection can be formed between the one or more of the device contacts 242 and one or more of the power source contacts 252 of the power source 250 when the substrate 230 is sealed to the wafer. At 410, a portion of the wafer and the substrate 230 can be removed to form the sealed package or packages, e.g., a plurality of sealed packages 210 can be singulated from the housing wafer and substrate. Any suitable technique or techniques can be utilized to remove portions of the wafer and substrate, e.g., laser cutting, mechanical cutting, etching, etc.

Figure 10:
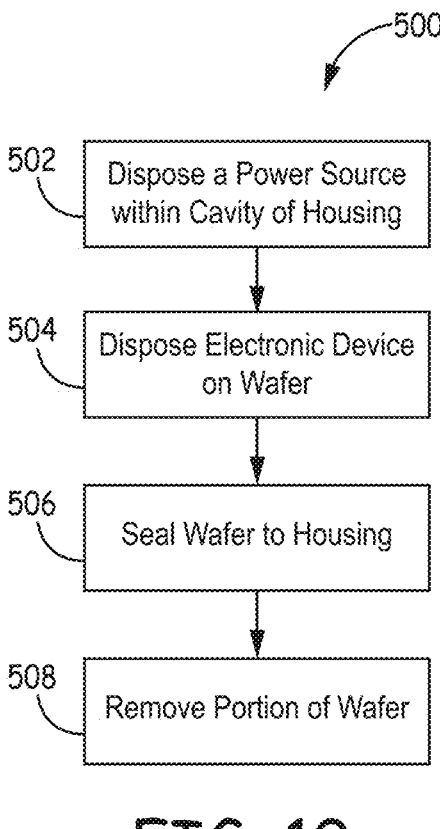
FIG. 10 is a flow chart of another embodiment of a method of forming a sealed package.

FIG. 10 is a schematic flow chart of another embodiment of a method 500 of forming a sealed package, e.g., sealed package 10 of FIGS. 1-4. At 502, power source 50 can be disposed within the cavity 26 of housing 20 using any suitable technique or combination of techniques. For example, in one or more embodiments, active material of the power source 50 can be sealed within a chamber formed in housing 20. One or more electronic devices 40 can be disposed on a major surface of a substrate wafer at 504. At 506, the major surface of the substrate wafer can be sealed to the housing 50 using any technique or combination of techniques, e.g., laser bonding the wafer to the housing. In one or more embodiments, the major surface of the substrate wafer can be hermetically sealed to the housing 50. Further, in one or more embodiments, a non-bonded electrical connection can be formed between one or more device contacts 42 of the electronic devices 40 and one or more power source contacts 52, 54 of the power source 50. At 508, one or more portions of the substrate wafer can be removed to form one or more packages, e.g., the one or more packages can be singulated from the substrate wafer using any suitable technique or combination of techniques.

Figure 11:
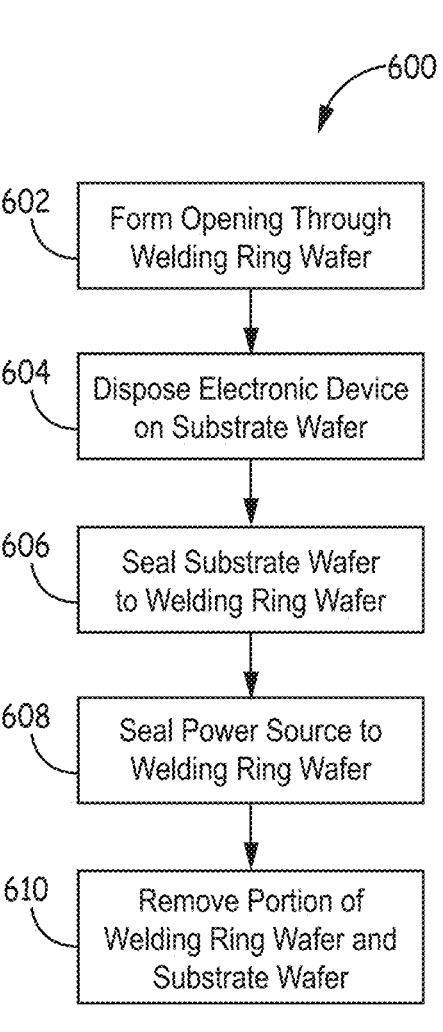
FIG. 11 is a flow chart of another embodiment of a method of forming a sealed package.
Figure 12:
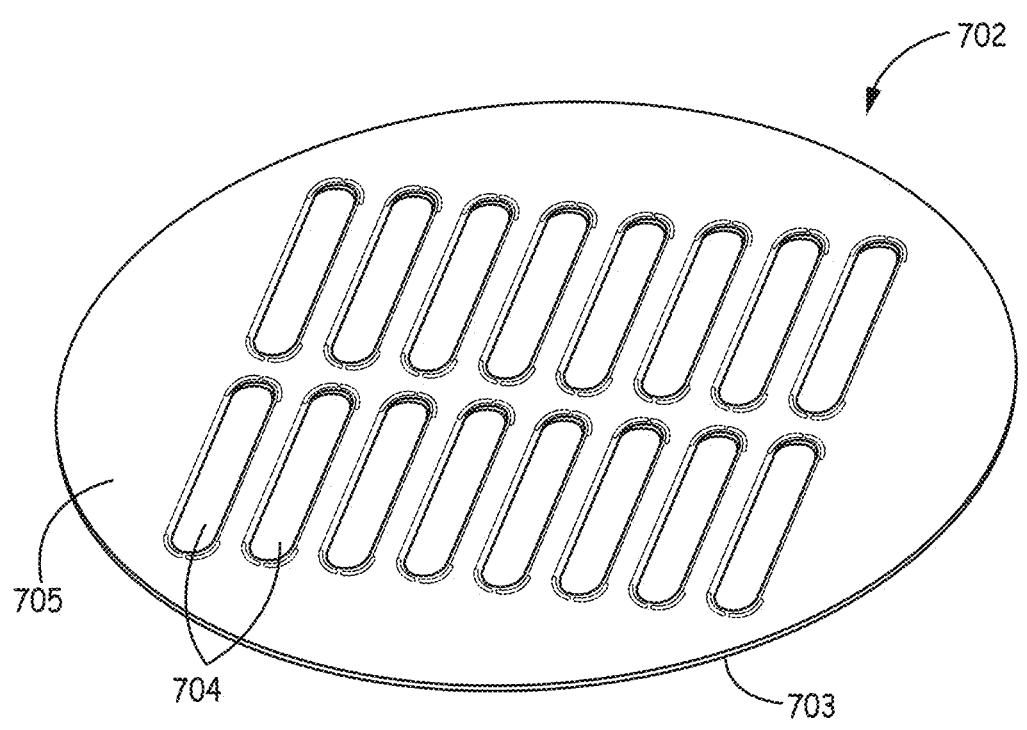
FIG. 12 is a schematic perspective view of one embodiment of a welding ring wafer.

FIG. 11 is a schematic flow chart of another embodiment of a method 600 for forming a sealed package, e.g., sealed package 10 of FIGS. 5-6. The method 600 includes forming an opening through a welding ring wafer at 602. Any suitable welding ring wafer can be utilized. For example, FIG. 12 is a schematic perspective view of a welding ring wafer 702. Any suitable material or combination materials can be utilized to form the welding ring wafer 702, e.g., the same materials described regarding welding ring 180 of package 100 of FIGS. 5-6. The welding ring wafer 702 includes a plurality of openings 704 formed through the wafer.

Figure 13:
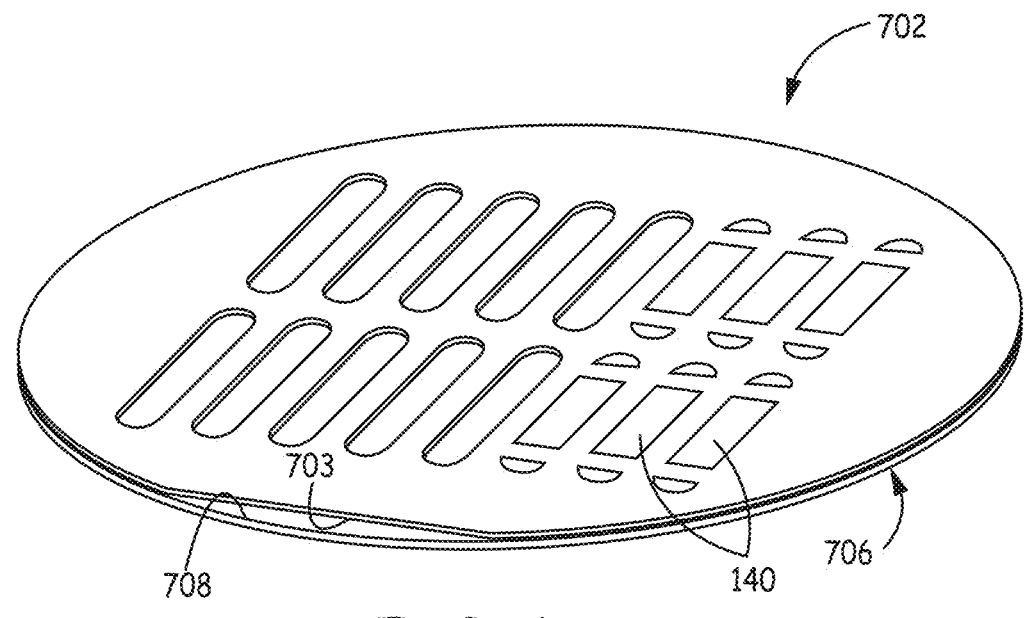
FIG. 13 is a schematic perspective view of one embodiment of a substrate wafer.

At 604, the method 600 further includes disposing one or more electronic devices 140 on a major surface 708 of a substrate wafer 706 as illustrated in FIG. 13. The substrate wafer 706 can include any suitable material or combination of materials, e.g., the same materials described regarding the substrate 30 of FIGS. 1-4. The electronic devices 140 can be disposed on any suitable major surface of the substrate wafer 706. At 606, the substrate wafer 706 can be sealed to the welding ring wafer 702 using any suitable technique or combination of techniques, e.g., laser bonding the substrate wafer to the welding ring wafer. Further, in one or more embodiments, the major surface 708 of the device substrate wafer 706 can be hermetically sealed to a first major surface 703 of the welding ring wafer 702. In one or more embodiments, the substrate wafer 706 can be sealed to the welding ring wafer 702 such that one or more electronic devices are registered within one or more openings 704 formed through the welding ring wafer 702. In one or more embodiments, a plurality of electronic devices can be disposed on the substrate wafer 706 such that one or more electronic devices 140 are registered with one or more openings of the plurality of openings 704. Any suitable number of electronic devices 140 can be disposed within each opening of the plurality of openings 704.

Figure 14:
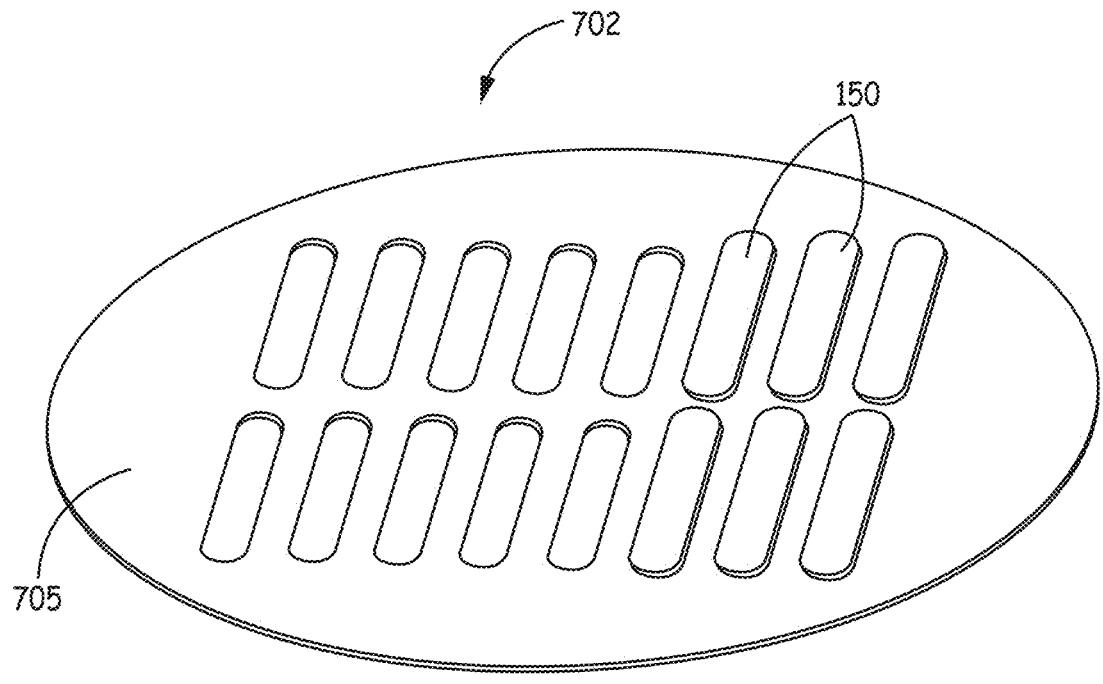
FIG. 14 is a schematic perspective view of the welding ring wafer of FIG. 12 having a plurality of power sources disposed thereon.

At 608, one or more power sources 150 can be sealed to a second major surface 705 of the welding ring wafer 702 as shown in FIG. 14 using any suitable technique or combination of techniques, e.g., laser bonding the one or more power sources to the second major surface of the welding ring wafer. In one or more embodiments, each power source 150 sealed to the welding ring wafer 702 can be registered with an opening of the plurality of opening 704 in the welding ring wafer 702. In one or more embodiments, one or more power sources 150 are hermetically sealed to the second major surface 705 of the welding ring wafer 702. Further, in one or more embodiments, a non-bonded electrical connection can be formed between one or more device contacts 142 of one or more electronic devices 140 and one or more power source contacts 152 of one or more power sources 150 when the major surface 703 of the device substrate 130 is sealed to the welding ring wafer 702.

At 610, one or more portions of the welding ring wafer 702 and substrate wafer 706 can be removed to form one or more sealed packages 100. Any suitable technique or combination of techniques can be utilized to remove one or more portions of the welding ring wafer 702 and the substrate wafer 706. In one or more embodiments, a portion or portions of the substrate wafer 706 can be removed prior to removal of portions of the welding ring wafer 702. One or more edges of the remaining portions of the substrate wafer 706 that form the substrate 130 for each package 100 can be rounded or smoothed. A portion or portions of the welding ring wafer 702 can be removed to singulate one or more packages 100 from the welding ring wafer using any suitable technique or combination of techniques. In one or more embodiments, one or more portions of the welding ring wafer 702 and substrate wafer 706 can be removed to form individual substrates that include one or more devices and a welding ring wafer prior to sealing a power source 150 to the welding ring of the individual substrate. In other words, the welding ring wafer 702 and substrate wafer 706 can be singulated prior to sealing one or more power sources 150 to singulated portions of the welding ring wafer and substrate wafer.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method of forming a hermetically-sealed package, comprising:
   disposing a power source at least partially within a housing;
   disposing an electronic device on a major surface of a substantially transparent substrate;
   hermetically sealing the substrate to the housing, wherein a non-bonded electrical connection is formed between a device contact of the electronic device and a power source contact of the power source when the substrate is hermetically sealed to the housing, wherein hermetically sealing the substrate to the housing comprises laser bonding the major surface of the substrate to the housing.

2. The method of claim 1, further comprising disposing one or more electrodes on a second major surface of the substrate.

3. The method of claim 2, further comprising:
   forming a via between the major surface and the second major surface of the substrate; and
   electrically connecting the one or more electrodes to the electronic device through the via.

4. The method of claim 1, wherein the housing further comprises a flange surrounding a cavity of the housing, wherein hermetically sealing the substrate to the housing comprises hermetically sealing the substrate to the flange of the housing.

5. The method of claim 1, wherein the electronic device is disposed in a cavity of the housing between the substrate and an inner surface of the housing when the substrate is hermetically sealed to the housing.

6. The method of claim 1, further comprising:
   disposing an antenna on a second major surface of the substrate; and
   electrically connecting the electronic device to the antenna.

7. The method of claim 6, wherein electrically connecting the electronic device to the antenna comprises forming a via between the major surface and the second major surface of the substrate such that the electronic device is electrically connected to the antenna through the via.

* * * * *